United States Patent
Gradel

(10) Patent No.: US 9,125,744 B2
(45) Date of Patent: Sep. 8, 2015

(54) METHOD FOR MANUFACTURING A PROSTHETIC HIP ACETABULUM

(75) Inventor: Thomas Gradel, Marignier (FR)

(73) Assignee: Inventorio SA, Gland (CH)

( * ) Notice: Subject to any disclaimer, the term of this patent is extended or adjusted under 35 U.S.C. 154(b) by 1 day.

(21) Appl. No.: 13/498,358

(22) PCT Filed: Sep. 27, 2010

(86) PCT No.: PCT/IB2010/054341
§ 371 (c)(1),
(2), (4) Date: Mar. 27, 2012

(87) PCT Pub. No.: WO2011/098868
PCT Pub. Date: Aug. 18, 2011

(65) Prior Publication Data
US 2012/0180300 A1    Jul. 19, 2012

(30) Foreign Application Priority Data
Sep. 28, 2009 (FR) .................................. 09 56715

(51) Int. Cl.
| | |
|---|---|
| *B23P 11/02* | (2006.01) |
| *A61F 2/32* | (2006.01) |
| *A61F 2/34* | (2006.01) |
| *A61F 2/46* | (2006.01) |
| *A61F 2/30* | (2006.01) |

(52) U.S. Cl.
CPC ................ *A61F 2/34* (2013.01); *A61F 2/4609* (2013.01); *A61F 2/3094* (2013.01); *A61F 2/4637* (2013.01); *A61F 2002/30077* (2013.01); *A61F 2002/30331* (2013.01); *A61F 2002/30426* (2013.01); *A61F 2002/4629* (2013.01); *A61F 2002/4693* (2013.01); *A61F 2220/0025* (2013.01); *A61F 2220/0033* (2013.01); *Y10T 29/49865* (2015.01)

(58) Field of Classification Search
USPC .............. 29/446, 447, 800; 623/22.24, 22.27, 623/22.28, 22.29
See application file for complete search history.

(56) References Cited

U.S. PATENT DOCUMENTS

| | | | | |
|---|---|---|---|---|
| 4,563,778 | A | * | 1/1986 | Roche et al. ................ 623/22.38 |
| 5,080,677 | A | * | 1/1992 | Shelley ....................... 623/22.24 |
| 5,431,657 | A | * | 7/1995 | Rohr .............................. 606/91 |

(Continued)

FOREIGN PATENT DOCUMENTS

| | | |
|---|---|---|
| DE | 3101333 A1 | 12/1981 |
| DE | 4403994 C1 | 10/1995 |

(Continued)

*Primary Examiner* — Essama Omgba
*Assistant Examiner* — Darrell C Ford
(74) *Attorney, Agent, or Firm* — William H. Eilberg

(57) ABSTRACT

A method for manufacturing a prosthetic hip acetabulum includes the following steps. First, one provides an insertion cup (1) having an inner concave receiving surface (3) having an opening surface (5) contained in an opening plane (P), and having an outer annular receiving structure (6). Next, one provides an installation and positioning insert (7) having a peripheral annular attachment structure (10) shaped to engage with the receiving surface (9) of the structure (6), fitting around that structure. Next, one heats the insert (7) in order to increase its size. Next, one fits the attachment structure (10) around the receiving surface (9) of the receiving structure (6). Finally, one cools the insert (7) to room temperature to reduce its size and achieve radial tightening of the attachment structure (10) on the outer annular receiving structure (6).

19 Claims, 9 Drawing Sheets

(56) References Cited

U.S. PATENT DOCUMENTS

| | | | |
|---|---|---|---|
| 5,486,181 A | 1/1996 | Cohen | |
| 5,888,205 A | 3/1999 | Pratt | |
| 6,132,469 A * | 10/2000 | Schroeder | 623/22.24 |
| 6,488,713 B1 * | 12/2002 | Hershberger | 623/22.11 |
| 6,589,284 B1 * | 7/2003 | Silberer | 623/22.29 |
| 6,682,567 B1 | 1/2004 | Schroeder | |
| 6,887,276 B2 * | 5/2005 | Gerbec et al. | 623/18.11 |
| 7,927,376 B2 * | 4/2011 | Leisinger et al. | 623/23.43 |
| 7,947,220 B2 * | 5/2011 | Lambert et al. | 422/1 |
| 8,556,985 B2 * | 10/2013 | Meridew | 623/22.36 |
| 8,679,187 B2 * | 3/2014 | Allen et al. | 623/22.24 |
| 8,679,188 B2 * | 3/2014 | Shea et al. | 623/22.28 |
| 8,764,843 B2 * | 7/2014 | Gradel | 623/22.12 |
| 8,801,797 B2 * | 8/2014 | Imhof | 623/22.24 |
| 2003/0050705 A1 * | 3/2003 | Cueille et al. | 623/22.24 |
| 2004/0019380 A1 * | 1/2004 | Baege et al. | 623/11.11 |
| 2004/0186586 A1 | 9/2004 | Seyer | |
| 2007/0122305 A1 * | 5/2007 | Lambert et al. | 422/4 |
| 2009/0005879 A1 * | 1/2009 | Tuke et al. | 623/22.24 |
| 2010/0087930 A1 * | 4/2010 | Tuke et al. | 623/22.21 |
| 2010/0262144 A1 * | 10/2010 | Kelman et al. | 606/62 |
| 2013/0091683 A1 * | 4/2013 | Gradel | 29/428 |
| 2013/0131823 A1 * | 5/2013 | Morrey et al. | 623/22.24 |
| 2013/0245781 A1 * | 9/2013 | Allen et al. | 623/22.28 |
| 2013/0268083 A1 * | 10/2013 | McMinn | 623/22.24 |
| 2014/0156018 A1 * | 6/2014 | Allen et al. | 623/22.12 |
| 2014/0180431 A1 * | 6/2014 | Conway et al. | 623/22.24 |
| 2014/0207245 A1 * | 7/2014 | McMinn | 623/22.24 |

FOREIGN PATENT DOCUMENTS

| | | |
|---|---|---|
| EP | 0931523 A1 | 7/1999 |
| EP | 1721586 A1 | 11/2006 |
| FR | 2830746 A1 | 4/2003 |
| FR | 2897527 A1 | 2/2006 |
| FR | 2876278 A1 | 4/2006 |
| FR | 2909541 A1 | 6/2008 |
| FR | 2916960 A1 | 12/2008 |
| WO | 2006040483 A1 | 4/2006 |
| WO | 2009098491 A1 | 8/2009 |
| WO | 2010146398 A1 | 12/2010 |

* cited by examiner

METHOD FOR MANUFACTURING A PROSTHETIC HIP ACETABULUM

TECHNICAL FIELD OF THE INVENTION

The present invention relates to a method for manufacturing a prosthetic acetabulum intended to replace the natural acetabulum of the hip.

A total hip prosthesis comprises two parts constituting a ball-and-socket joint, namely a female part intended to replace the natural acetabulum of the hip, and a male part intended to replace the head of the femur. The male part of the joint generally has a shaft which is intended to engage in the medullary canal of the femur and of which the proximal end is connected by a neck to a spherical head intended to engage in the female part. The female part of the joint, which has to replace the natural acetabulum of the hip, usually comprises a substantially hemi-spherical insertion cup, which is accommodated in a prepared acetabular cavity in the pelvic bone. The insertion cup is usually made of metal.

When fitting the insertion cup in the acetabular cavity, it must be possible to use an impactor for holding and manipulating the insertion cup and for applying a force to drive the cup into the acetabular cavity in the bone with a good orientation and for long enough for a cement to set between the outer surface of the insertion cup and the acetabular cavity of the bone.

The document FR 2 909 541 A1 describes an insertion cup with a convex and hemispherical outer anchoring face. To hold this cup during its impaction, an outer annular groove is provided near its free annular edge. This annular groove permits the fixation of an impactor comprising a main body with at least two hook-shaped elastic tabs.

In this document, the force with which the cup is retained by the impactor is in correlation with and substantially equal to the force that has to be applied to spread apart the elastic tabs. This means that the better the hold of the cup by the impactor, the more difficult it is to spread the tabs apart, and this causes the user more effort to fix the impactor to the cup.

There is a need to permit easy fixation of an impactor to a cup while providing a reliable hold of the cup.

The document WO 2006/040483 A1 describes a prosthetic hip acetabulum comprising an insertion cup with:
 a substantially hemispherical convex outer anchoring face designed to be anchored in an acetabular cavity of the pelvis of a patient,
 a concave inner receiving face with an annular edge and with an opening face that is contained in an opening plane,
 an annular receiving structure designed in such a way that an impactor can be fixed to said annular receiving structure for impaction of the cup in the acetabular cavity of the pelvis of a patient.

In the document WO 2006/040483 A1, the installation and orientation insert is cooled so as to contract and permit its introduction into the insertion cup, and it is then brought back to room temperature in order to expand and attach itself strongly to the insertion cup. In order to sufficiently reduce the dimensions of the installation and orientation insert, the latter is cooled in a refrigerated vessel. The presence of liquid has sometimes been observed inside the refrigerated vessel, resulting from a condensation phenomenon. Condensate liquids contaminated by bacteria or microbes can thus form and/or settle on the installation and orientation insert, which then contaminates the insertion cup after the installation and orientation insert and the insertion cup have been joined together. This is particularly critical when the installation and orientation insert is made of plastic: the plastics that can be used for the installation and orientation insert, for example polyethylene, have a tendency to absorb the liquids. There is therefore a risk that the installation and orientation inserts made of plastic will absorb condensate liquids contaminated by bacteria or microbes, which then causes deep-rooted contamination of the installation and orientation inserts.

Moreover, it is also expedient to provide, between the cup and the impactor, a stronger join than is made possible by the teaching of the document WO 2006/040483 A1.

SUMMARY OF THE INVENTION

A problem addressed by the invention is that of making available a method for manufacturing a prosthetic hip acetabulum with insertion cup that can be fixed more reliably and more firmly to an impactor, while limiting the forces to be applied and avoiding any risk of contamination.

To achieve these objects, and others, the invention proposes a manufacturing method comprising the steps of:
 a) providing an insertion cup having a concave inner receiving face with an opening face contained in an opening plane, and having an outer annular receiving structure,
 b) providing an installation and orientation insert having a peripheral annular fixing structure designed to cooperate with the receiving face of the outer annular receiving structure by engaging around the outer annular receiving structure,
 c) heating the installation and orientation insert in order to increase the dimensions thereof,
 d) engaging the peripheral annular fixing structure around the receiving face of the outer annular receiving structure,
 e) bringing the installation and orientation insert back to room temperature in order to reduce the dimensions thereof, so as to achieve a radial clamping of the peripheral annular fixing structure on the outer annular receiving structure.

Such a manufacturing method makes it possible to obtain satisfactory radial clamping of the installation and orientation insert on the insertion cup.

The engagement of the installation and orientation insert around the outer annular receiving structure takes place without too much force, on account of the expansion of the installation and orientation insert by heating.

However, the separation of the cup and the installation and orientation insert requires substantial forces after cooling, and this permits satisfactory impaction and orientation of the cup.

The forced retention of the installation and orientation insert on the insertion cup by radial clamping ensures reliable and secure fixation, by means of which it is possible to withstand the forces applied during the impaction of the insertion cup. The radial clamping of the peripheral annular fixing structure on the outer annular receiving structure makes it possible to achieve this reliable fixation without over-complicating the shape of the outer annular receiving structure.

The retention of the installation and orientation insert on the insertion cup is more reliable than that of document WO 2006/040483 A1, especially by virtue of the fact that the radial clamping takes place on an annular receiving structure which is external and which thus has a greater contact surface with the installation and orientation insert.

Finally, the radial clamping of the peripheral annular fixing structure on the outer annular receiving structure induces a state of prestressing in the insertion cup, and this prestressing limits the risks of deformation of the insertion cup during its impaction in the acetabulum of the pelvis of a patient. The reason is that, when the insertion cup has a relatively small thickness near its upper annular edge, for example of less than 3 mm, phenomena of ovalization of the insertion cup sometimes occur (if the insertion cup is made of a deformable material such as metal or plastic for example), and these phenomena then make it impossible for the male part of the prosthetic joint to engage in the insertion cup, or they generate unequally distributed internal mechanical stresses likely to lead to the breakage of the insertion cup (if the latter is made of a weak material such as ceramic for example) or generate unequally distributed internal mechanical stresses likely to subsequently damage the articular insert, especially if the latter is made of ceramic.

In the manufacturing method of the present invention, by means of providing an insertion cup having an outer annular receiving structure on which an installation and orientation insert is clamped by being brought back to room temperature after expansion by heating, it is possible to avoid the problem of contamination of the installation and orientation inserts, especially when these are made of polyethylene.

Within the context of the present invention, the concave inner receiving face can be a slide face for receiving an articular insert that is movable with respect to the insertion cup (for an acetabulum with dual mobility for example) or can be designed to receive an articular insert that is stationary with respect to the insertion cup (for an acetabulum with single mobility for example).

Advantageously, before fixing the installation and orientation insert on the insertion cup, the method can comprise the supplementary step b1) of inserting an articular insert in the concave inner receiving face of the insertion cup.

The insertion cup, the articular insert and the installation and orientation insert can thus be pre-assembled at the place of manufacture, such that the surgeon simply has to impact the unit thus formed without having to concern himself with the articular insert. In addition, the articular insert can then be positioned correctly in the insertion cup without any involvement of the surgeon. This therefore limits the risks of poor positioning of the articular insert in the insertion cup, which can lead to premature breaking of the articular insert.

Advantageously, provision can be made that:
the articular insert is made of ceramic,
the installation and orientation insert has elastic means for holding the articular insert in the insertion cup,
when the installation and orientation insert is fixed to the insertion cup, the installation and orientation insert comes into contact with the articular insert only via the elastic means for holding the articular insert in the insertion cup.

The elastic holding means keep the articular insert correctly positioned in the insertion cup during transport and storage and when being handled by the surgeon. When the surgeon applies an impaction force on the insertion cup by way of the installation and orientation insert, no shock will be transferred to the ceramic articular insert, since the elastic holding means will deform. There is therefore no risk of the surgeon breaking the ceramic articular insert during the impaction.

Advantageously, the method can additionally have a step f) during which the unit thus formed and packed in a microbial protection envelope is sterilized.

Preferably, provision can be made that the articular insert is made of ceramic, and that the step f) of sterilization is carried out by bombardment with gamma rays, advantageously at a dose of between approximately 25 kGy and approximately 40 kGy.

In the document WO 2006/040483 A1, the annular receiving structure comprises a cylindrical or slightly conical annular retention surface that continues the surface of the concave inner receiving face.

However, this substantially cylindrical continuation limits the possible angular clearance of the prosthetic femoral shaft. In addition, the cylindrical continuation increases the risk that the prosthetic femoral shaft, which is generally made of metal, comes into contact with the insertion cup. In the event of such contact, if the insertion cup is made of metal, a phenomenon of metallosis occurs through degradation of the edge of the insertion cup and/or of the prosthetic femoral shaft. This degradation produces metal debris that can impregnate the surrounding tissues and/or damage the prosthesis. Moreover, when the cup is not made of metal, and is in particular made of ceramic or a plastic such as PEEK for example, there is a risk of partial or total breakage of the insertion cup.

This is why the annular receiving structure can preferably be external and be situated set back from the opening plane.

When the annular receiving structure for fixation of the impactor is situated set back from the opening plane, in the direction of the summit of the substantially hemispherical convex outer anchoring face, this annular receiving structure no longer limits the angular clearance of the prosthetic femoral shaft that will be fitted. At the same time, the risk of contact between the prosthetic femoral shaft and the edge of the insertion cup is limited, thereby reducing the risk of metallosis and/or breakage.

Preferably, the installation and orientation insert can have an assembly structure on which an impactor can be fixed removably.

It is thus possible to mount the installation and orientation insert on the insertion cup at the place of manufacture, such that the surgeon then simply has to fix the impactor on the installation and orientation insert in order to perform impaction of the insertion cup. There is no risk of the surgeon damaging the concave inner receiving face of the insertion cup, the latter being protected by the installation and orientation insert.

Advantageously, provision can be made that:
the outer annular receiving structure comprises a continuous or interrupted peripheral radial shoulder of the annular edge, with a receiving face directed toward the outside,
the installation and orientation insert has a continuous or interrupted peripheral annular fixing structure with a connecting face directed toward the inside and designed to cooperate with the receiving face of the outer annular receiving structure.

According to a first variant, provision can be made that:
the receiving face of the outer annular receiving structure has an interrupted peripheral locking groove,
the connecting face of the peripheral annular fixing structure of the installation and orientation insert has a plurality of locking ribs distributed peripherally and designed so as to engage in the interrupted peripheral locking groove.

According to a second variant, provision can be made that:
either the receiving face of the outer annular receiving structure or the connecting face of the peripheral annular fixing structure has a continuous peripheral annular locking groove, the other of the connecting face of the peripheral annular fixing structure or the receiving face of the outer annular receiving structure has a continuous or interrupted peripheral annular locking rib designed so as to engage in the continuous peripheral annular locking groove.

The locking groove and the one or more locking ribs participate in retaining the installation and orientation insert on the insertion cup. This also greatly increases the strength of the join between the installation and orientation insert and the insertion cup in order to withstand orientation torques that the surgeon transfers by way of the impactor.

Advantageously, provision can be made that:
the peripheral radial shoulder of the annular edge has a thickness of between approximately 0.7 mm and approximately 1.2 mm,
said interrupted peripheral locking groove or said continuous peripheral annular locking groove of the outer annular receiving structure has a radial thickness of between approximately 0.2 mm and approximately 0.6 mm.

Such dimensions are compatible with an insertion cup having a small thickness near its upper annular edge, for example of less than 3 mm. The use of an insertion cup having a small thickness near its upper annular edge makes it possible to increase the diameter of the spherical head of the male part of the joint and thus limit the risk of dislocation.

Preferably, provision can be made that the peripheral radial shoulder of the annular edge has a height of between approximately 1 mm and approximately 4 mm.

Such a height of the peripheral radial shoulder provides a sufficient contact surface between the installation and orientation insert and the insertion cup for the radial clamping, without thereby excessively diminishing the surface area of the convex outer anchoring face intended to come into contact with the bone. This is all the greater in view of the fact that the outer anchoring surface part situated substantially in the vicinity of the equatorial plane thereof is a part that participates substantially in the retention of the insertion cup in the acetabular cavity of the pelvis.

Advantageously, provision can be made that said interrupted peripheral locking groove or said continuous peripheral annular locking groove of the outer annular receiving structure has a height of between approximately 0.4 mm and approximately 3 mm.

Preferably, provision can be made that the installation and orientation insert and the outer annular receiving structure of the insertion cup are designed in such a way that, when the installation and orientation insert is fixed on the outer annular receiving structure of the insertion cup, the installation and orientation insert does not protrude outside a substantially hemispherical surface defined by the substantially hemispherical convex outer anchoring face of the insertion cup. This therefore avoids any risk of conflict of the installation and orientation insert with the bone substance present near the prepared acetabular cavity of the pelvis of the patient.

Advantageously, the peripheral annular fixing structure of the installation and orientation insert can have a radial thickness substantially equal to or less than the thickness of the radial shoulder of the annular edge.

Preferably, the installation and orientation insert can be made of polyethylene. Polyethylene is commonly used in the medical field and is inexpensive and easy to machine. Moreover, polyethylene does not risk damaging an insertion cup made of metal, of ceramic, of PEEK or of a material harder than polyethylene.

Preferably, the assembly structure can comprise a fixation hole with internal thread made in the installation and orientation insert, permitting the screwing of a corresponding threaded portion of the impactor.

Advantageously, the fixation hole can be a through-hole able to cooperate with a disconnecting tool that has a threaded rod able to be screwed into the through-hole and which has a distal end designed to bear, directly or indirectly, against the concave inner receiving face of the insertion cup when the threaded rod is screwed into the through-hole.

Preferably, provision can be made that:
the installation and orientation insert is designed in such a way that a free space remains between the installation and orientation insert and the bottom of the concave inner receiving face, or, if appropriate, between the installation and orientation insert and the articular insert, once the installation and orientation insert is fixed to the outer annular receiving structure of the insertion cup,
the installation and orientation insert bears in a sealed manner across its connecting face against the receiving face of the outer annular receiving structure,
the fixation hole is a through-hole via which the free space between the installation and orientation insert and the bottom of the concave inner receiving face or, if appropriate, between the installation and orientation insert and the articular insert is brought into communication with the outside and which is dimensioned for leaktight engagement of the end of a syringe.

BRIEF DESCRIPTION OF THE DRAWINGS

Other subjects, features and advantages of the present invention will become clear from the following description of particular variants, said description making reference to the attached figures, in which.

Figure 1:
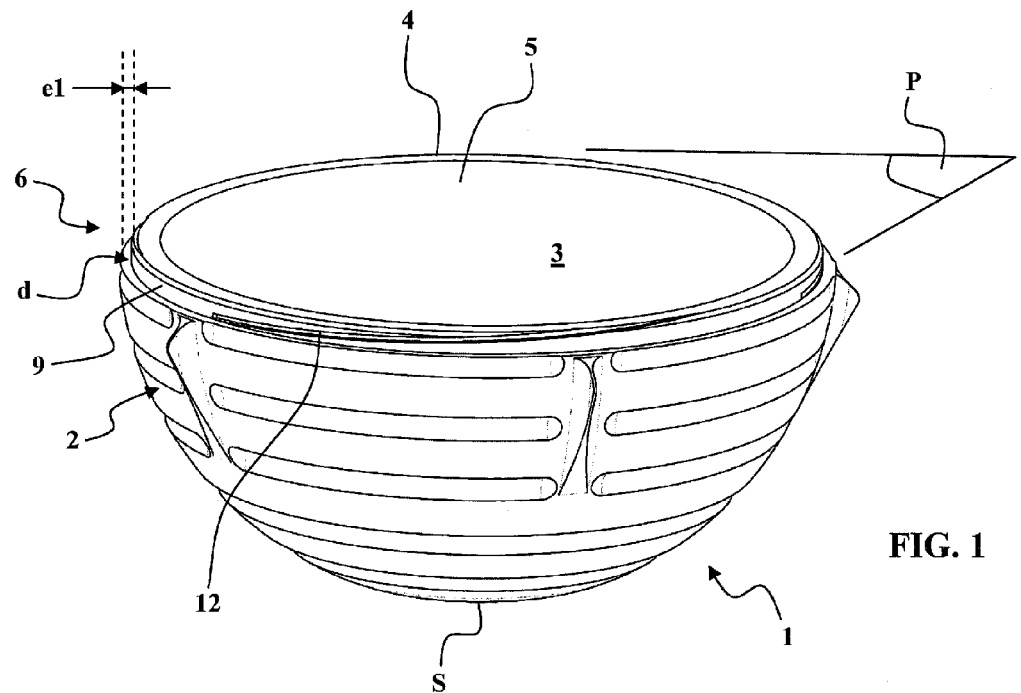
Figure 2:
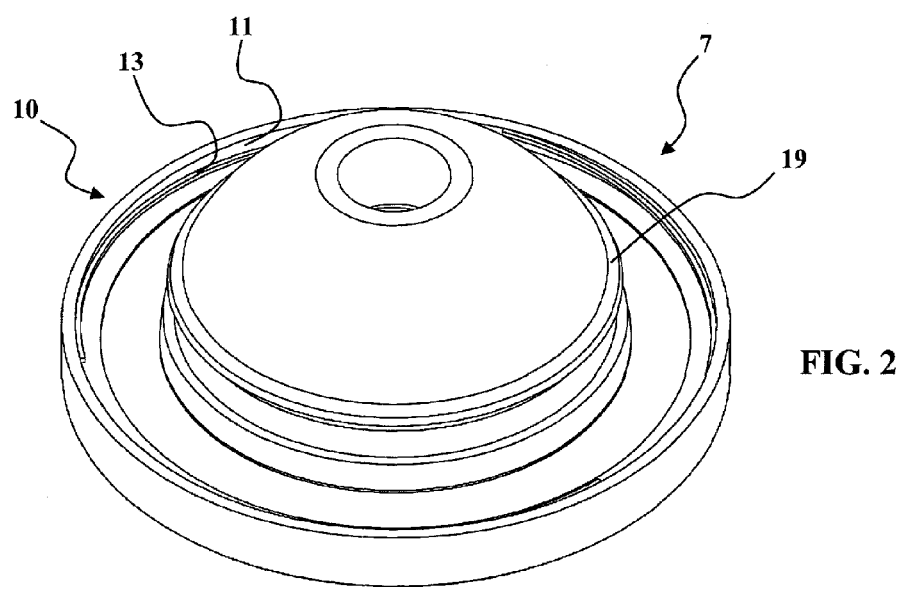
Figure 3:
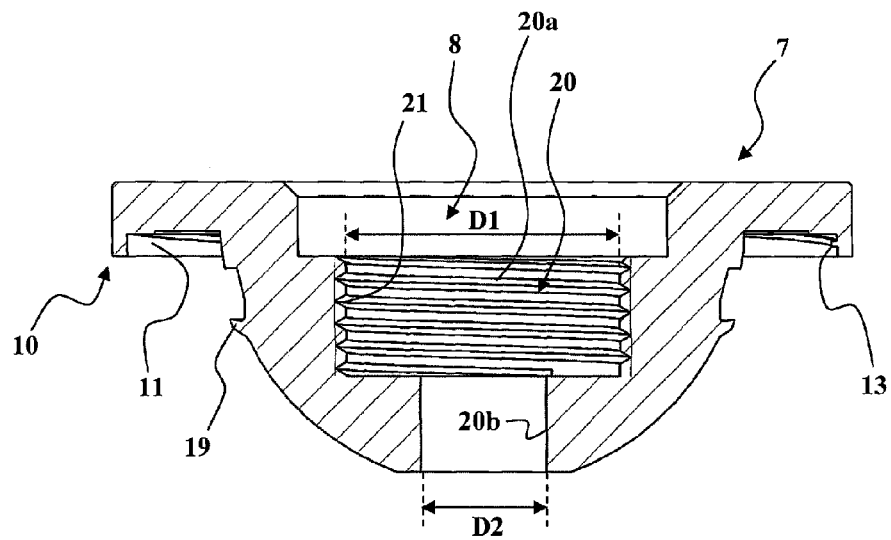
Figure 4:
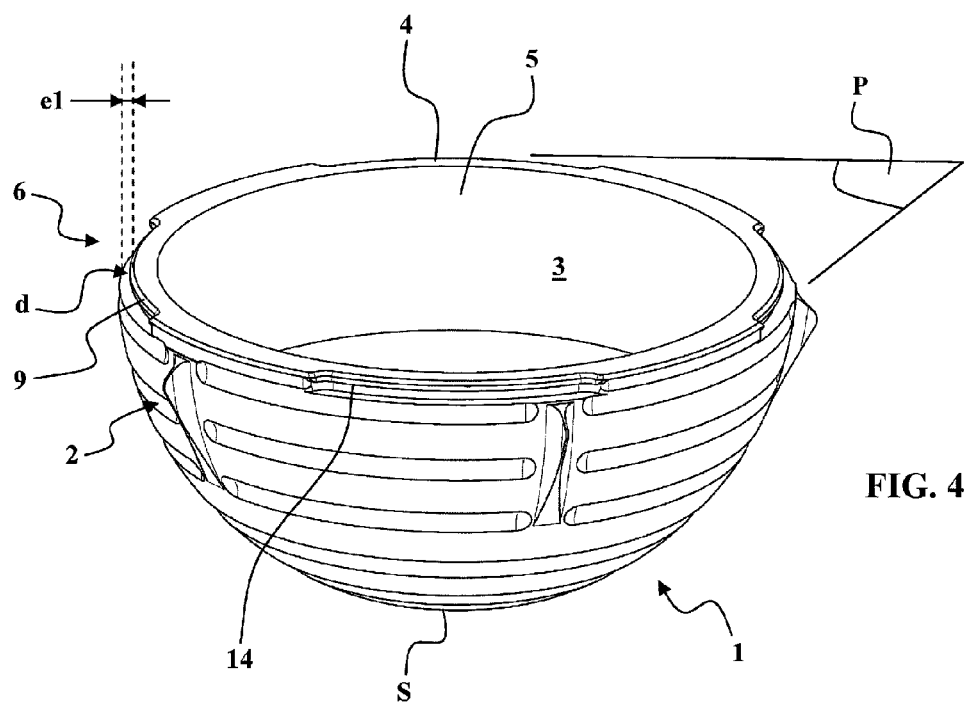
FIG. 4 is a perspective view of an insertion cup of a prosthetic acetabulum according to a first variant of the invention.

Some of the attached figures illustrate subject matter that is not part of the present invention but that is described below and that may form the subject of independent protection. These figures are the following:

FIG. 1, which is a perspective view of an insertion cup of a prosthetic acetabulum;

FIG. 2, which is a perspective view of an installation and orientation insert intended to be joined to the insertion cup from FIG. 1; and FIG. 3, which is a sectional view of the installation and orientation insert from FIG. 2.

DESCRIPTION OF PREFERRED
EMBODIMENTS

Each one of FIGS. 1, 4, 5 and 8 shows an insertion cup 1 of a prosthetic hip acetabulum. This insertion cup 1 comprises:
- a substantially hemispherical convex outer anchoring face 2, designed to be anchored in a prepared acetabular cavity of the pelvis of a patient, and a concave inner receiving face 3, with an annular edge 4 and with an opening face 5 that is contained in an opening plane P,
- an annular receiving structure 6 designed in such a way that an impactor can be fixed to said annular receiving structure 6 for the impaction of the insertion cup 1 in the acetabular cavity of the pelvis of a patient.

The annular receiving structure 6 is external and is situated set back from the opening plane P. In other words, the annular receiving structure 6 is offset, with respect to the opening plane P, in the direction of the summit S of the outer anchoring face 2.

The annular receiving structure 6 is therefore not situated in the continuation of the inner receiving face 3 continuing the latter past the summit S. It is thus possible to avoid limiting the angular clearance of the prosthetic femoral shaft, and the risk of metallosis and/or breakage is reduced.

Figure 5:
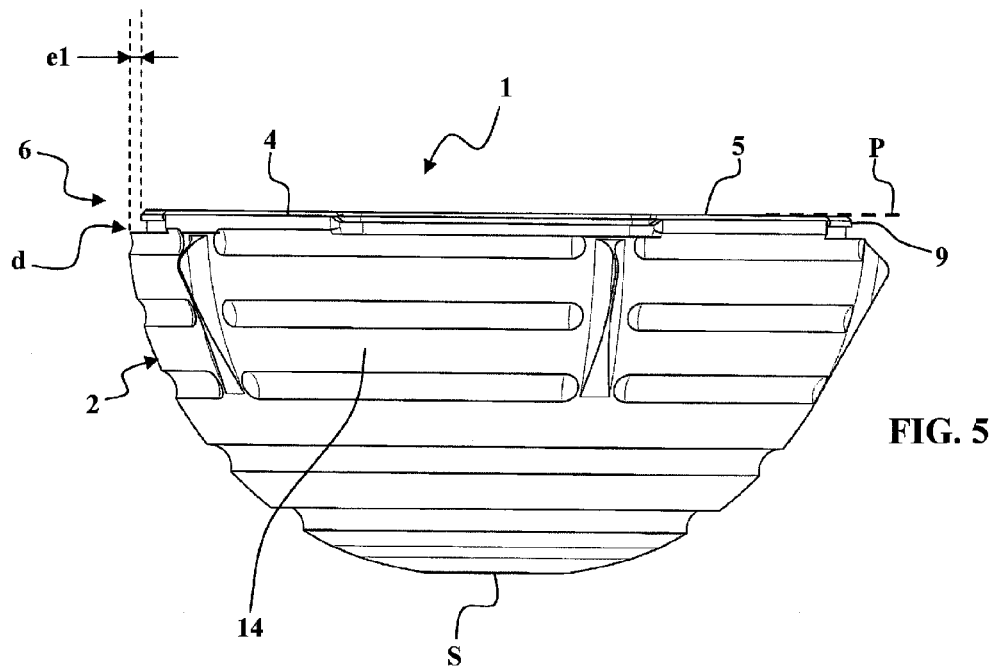
FIG. 5 is a side view of the cup from FIG. 4.
Figure 6:
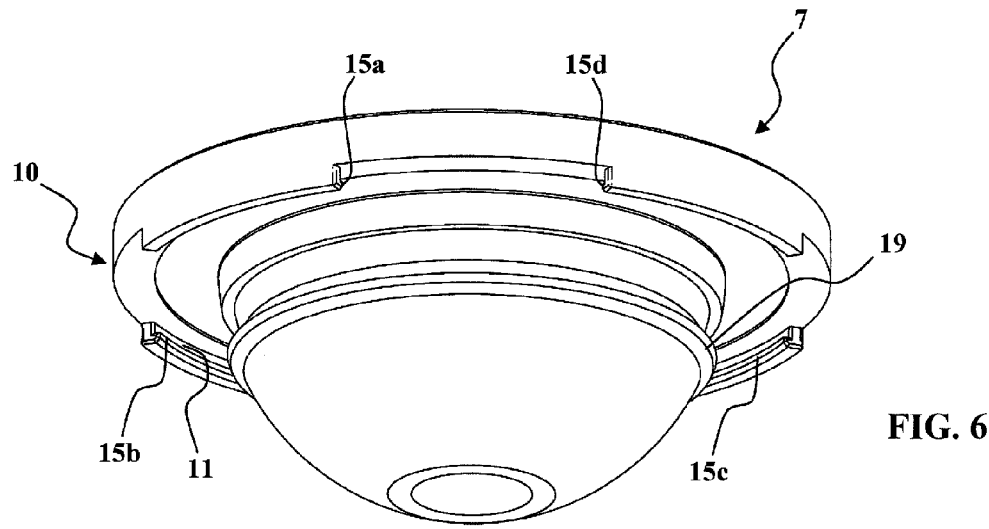
FIG. 6 is a perspective view of an installation and orientation insert intended to be joined to the insertion cup from FIGS. 4 and 5.
Figure 7:
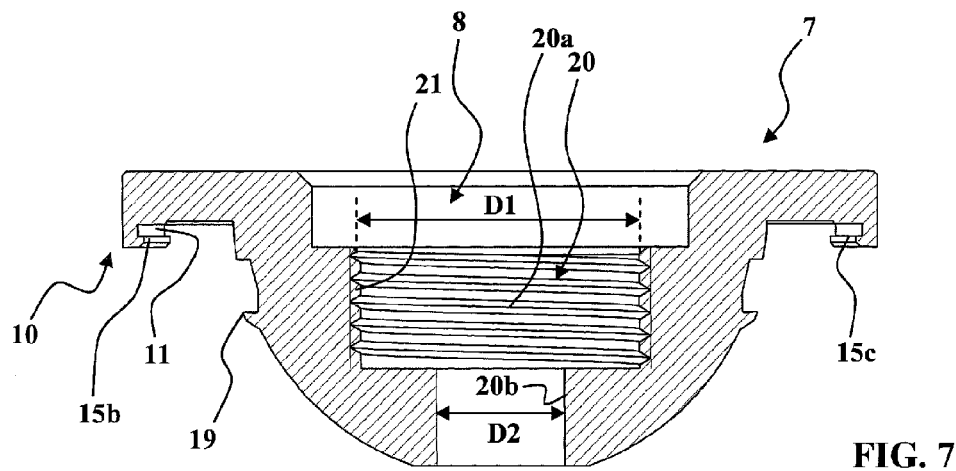
FIG. 7 is a sectional view of the installation and orientation insert from FIG. 6.
Figure 8:
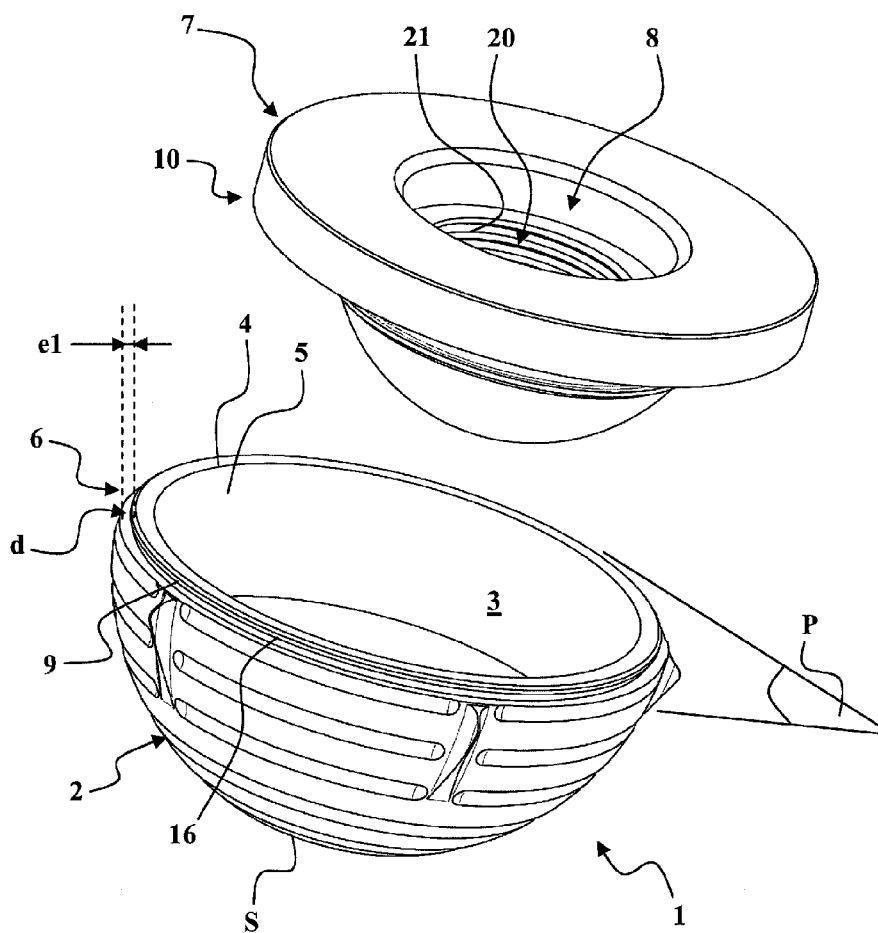
FIG. 8 is a perspective view of an installation and orientation insert and of an insertion cup of a prosthetic hip acetabulum according to a second variant of the invention.
Figure 9:
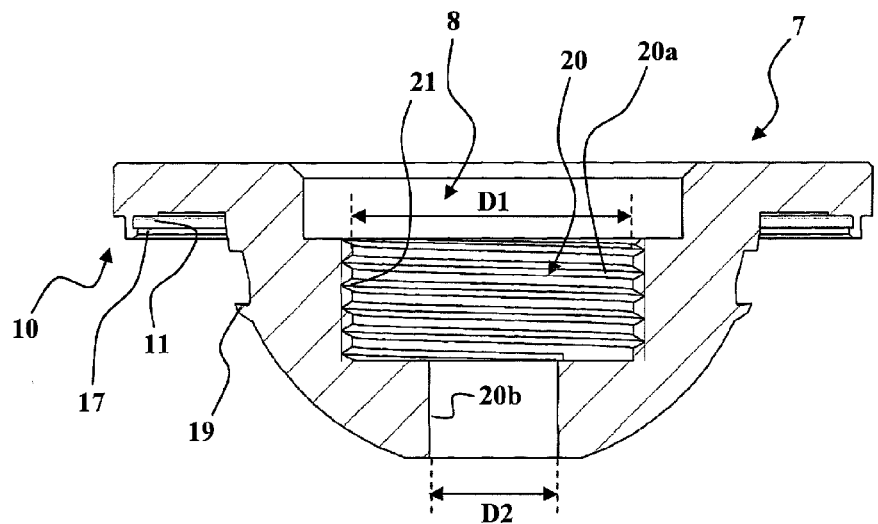
FIG. 9 is a sectional view of the installation and orientation insert from FIG. 8.

FIGS. 2, 3, 6, 7 and 9 show an installation and orientation insert 7 intended to be joined to an insertion cup 1. The installation and orientation insert 7 of FIGS. 2 and 3 is intended to be joined to the insertion cup 1 from FIG. 1. The installation and orientation insert 7 of FIGS. 6 and 7 is intended to be joined to the insertion cup 1 from FIGS. 4, 5 and 8. The installation and orientation insert 7 of FIG. 9 is intended to be joined to the insertion cup 1 from FIG. 8.

Each installation and orientation insert 7 can be fixed removably to the outer annular receiving structure 6 of the insertion cup 1 and has an assembly structure 8 on which an impactor can be removably fixed.

In FIGS. 1, 5 and 8, it will be seen that the outer annular receiving structure 6 comprises a continuous or interrupted peripheral radial shoulder d of the annular edge 4, with a receiving face 9 directed toward the outside. It will be seen in FIGS. 2, 3, 6, 7 and 9 that each installation and orientation insert 7 has a continuous or interrupted peripheral annular fixing structure 10 with a connecting face 11 directed toward the inside and designed to cooperate with the receiving face 9 of the outer annular receiving structure 6.

In the subject matter of FIGS. 1 to 3, the receiving face 9 of the outer annular receiving structure 6 has an external thread 12, while the connecting face 11 of the peripheral annular fixing structure 10 of the installation and orientation insert 7 has an internal thread 13 designed to cooperate with the external thread 12 by screwing.

The subject matter of the present invention is illustrated in FIGS. 4 to 13. In these figures, the outer annular receiving structure 6 and the peripheral annular fixing structure 10 are designed in such a way that the installation and orientation insert 7 is engaged with force around the outer annular receiving structure 6 and is retained forcibly by a radial clamping of the peripheral annular fixing structure 10 on the outer annular receiving structure 6.

In order to further improve the hold of the installation and orientation insert 7 on the insertion cup 1, a supplementary cooperation can be provided between the installation and orientation insert 7 and the insertion cup 1 by means of one or more locking ribs that engage in a locking groove.

In a first variant, illustrated in FIGS. 4 to 7, provision is made that:
- the receiving face 9 of the outer annular receiving structure 6 has an interrupted peripheral locking groove 14;
- the connecting face 11 of the peripheral annular fixing structure 10 of the installation and orientation insert 7 has a plurality of locking ribs 15a to 15d which are distributed about the periphery and are designed so as to engage in the interrupted peripheral locking groove 14.

In a second variant, illustrated in FIGS. 8 and 9, the receiving face 9 of the outer annular receiving structure 6 has a continuous peripheral annular locking groove 16, while the connecting face 11 of the peripheral annular fixing structure 10 has a continuous peripheral annular locking rib 17 designed so as to engage in the continuous peripheral annular locking groove 16.

In this second variant, it is also possible that the connecting face 11 of the peripheral annular fixing structure 10 has an interrupted peripheral annular locking rib. The installation and orientation insert 7 can then be similar to that of the first variant of the second embodiment of the invention, illustrated in FIGS. 6 and 7.

Figure 10:
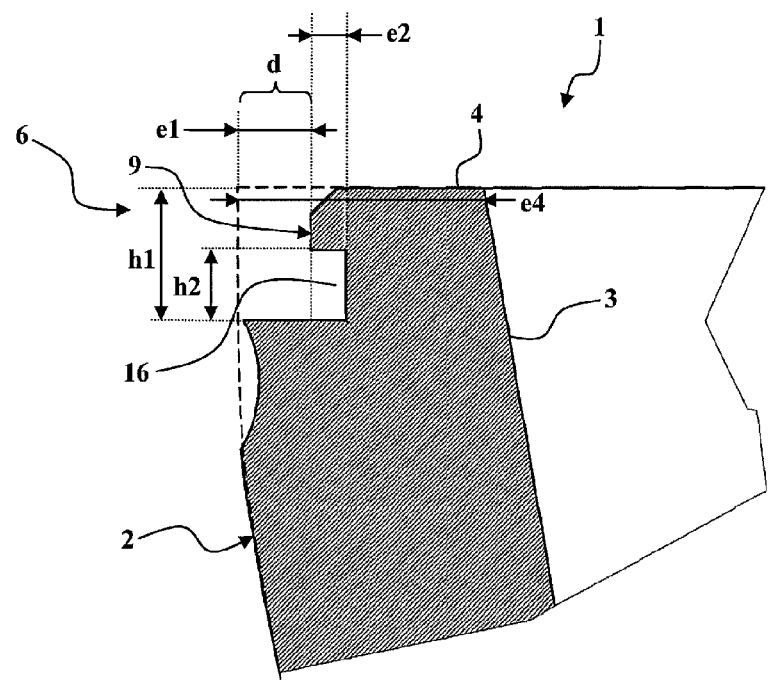
FIG. 10 is a partial sectional view of the insertion cup from FIG. 8.

FIG. 10 is a partial sectional view of the annular edge 4 of the insertion cup 1 from FIG. 8. It will be seen more particularly in FIG. 10 that the outer annular receiving structure 6 comprises a peripheral radial shoulder d with a receiving face 9 directed toward the outside. The peripheral radial shoulder d has a thickness e1 of between approximately 0.7 mm and approximately 1.2 mm.

The receiving face 9 has the continuous peripheral annular locking groove 16. The continuous peripheral annular locking groove 16 has a radial thickness e2 of between approximately 0.2 mm and approximately 0.6 mm.

The insertion cup 1 has a thickness e4 near its annular edge 4. The thickness e4 can be small, for example less than 3 mm.

The peripheral radial shoulder d of the annular edge 4 has a height h1 of between approximately 1 mm and approximately 4 mm.

Finally, the continuous peripheral annular locking groove 16 has a height h2 of between approximately 0.4 mm and 3 mm.

All the dimensions given above in connection with the second variant are valid for the first variant and also for the subject matter of FIGS. 1 to 3.

Figure 11:
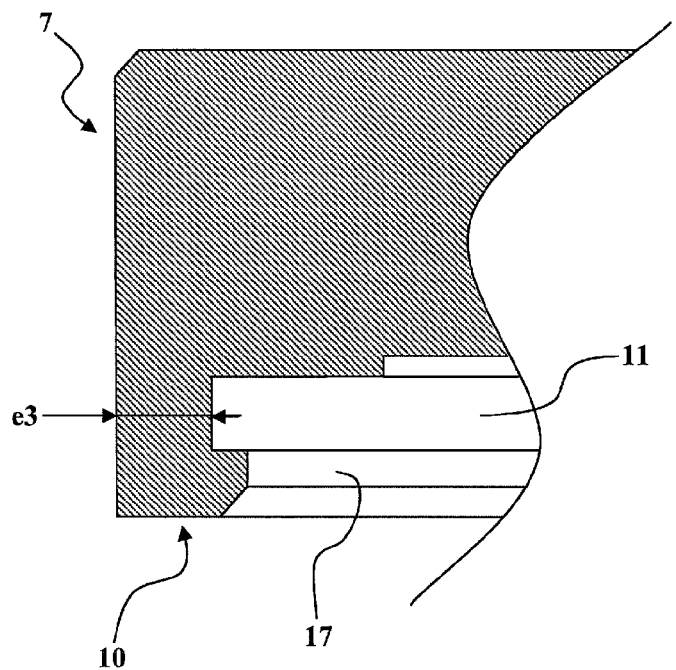
FIG. 11 is a partial sectional view of the installation and orientation insert from FIG. 9.
Figure 12:
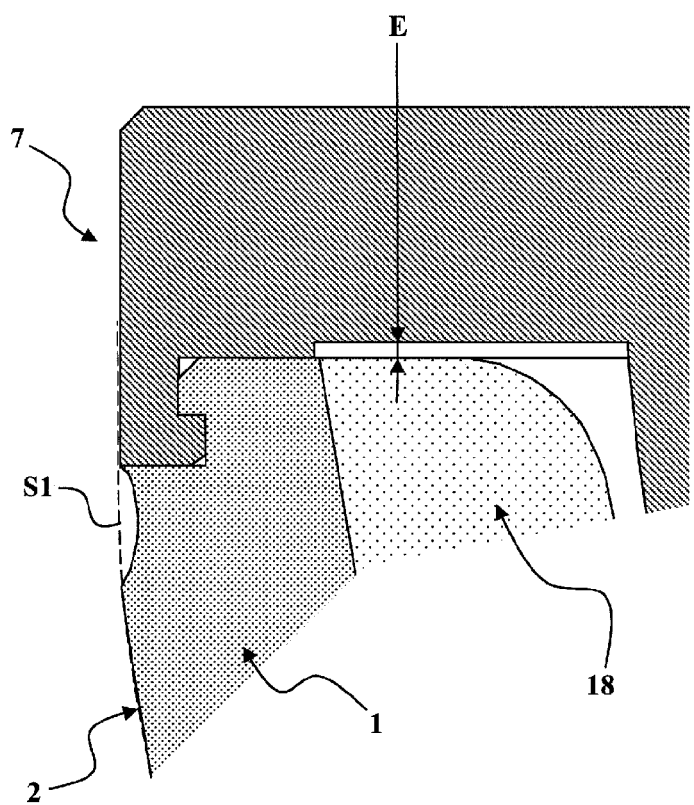
FIG. 12 is a partial sectional view of the insertion cup and of the installation and orientation insert from FIGS. 10 and 11.
Figure 13:
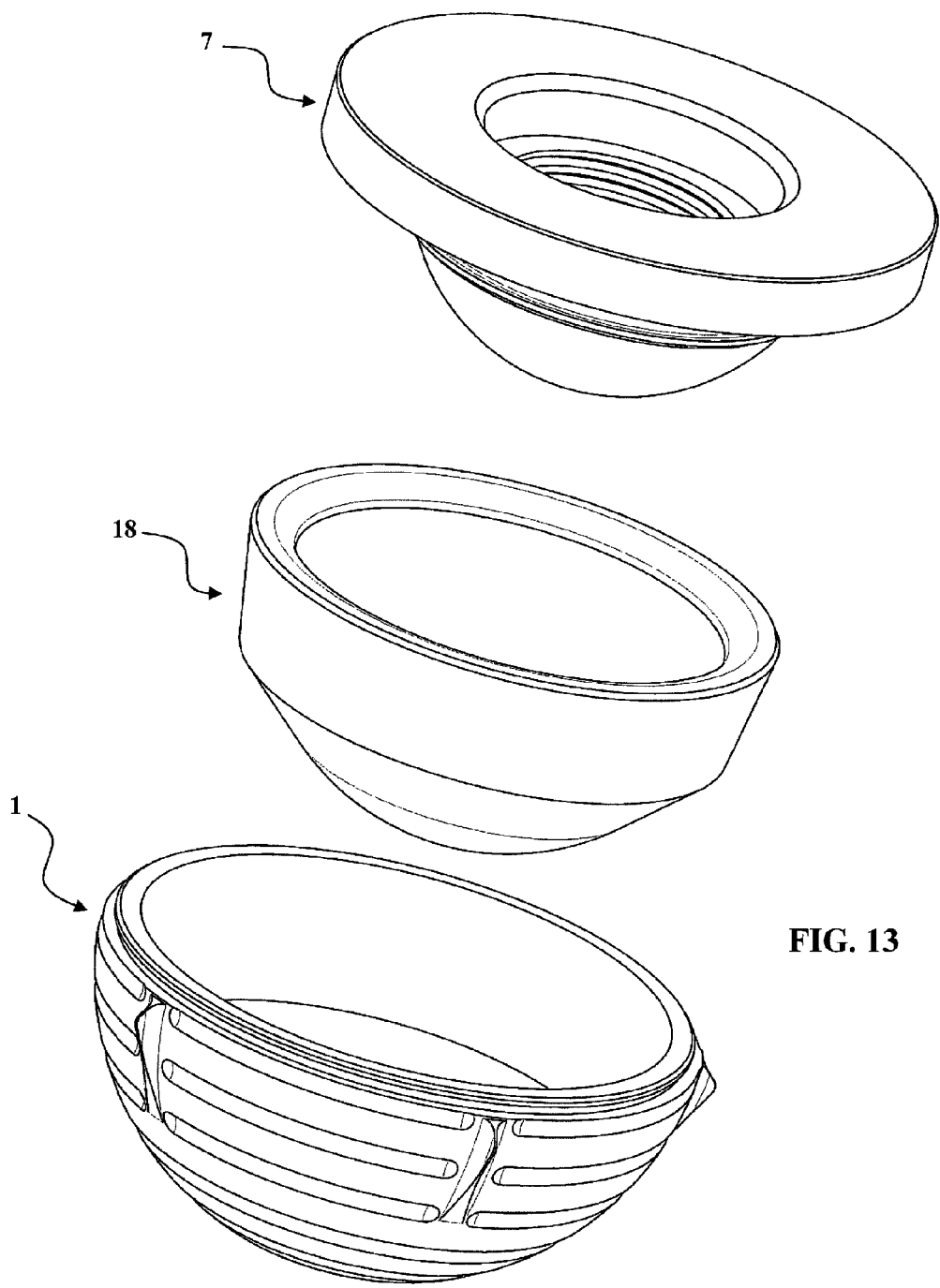
FIG. 13 is a perspective view of the insertion cup and of the installation and orientation insert from FIG. 8, with a stationary articular insert.

As will be seen from FIG. 11, the peripheral annular fixing structure 10 of the installation and orientation insert 7 has, with its connecting face 11 and its continuous peripheral annular locking rib 17, a shape and dimensions matching the receiving face 9 and the continuous peripheral annular locking groove 16. The installation and orientation insert 7 and the insertion cup 1 can thus be joined very intimately, as is illustrated in FIG. 12.

In order to avoid any conflict of the installation and orientation insert 7 with the bone substance around the natural acetabular cavity of the pelvis of the patient, the installation and orientation insert 7 and the outer annular receiving structure 6 of the insertion cup 1 are designed in such a way that, when the installation and orientation insert 7 is fixed to the outer annular receiving structure 6 of the insertion cup 1, the installation and orientation insert 7 does not protrude outside a substantially hemispherical surface S1 (illustrated by broken lines in FIG. 12) defined by the substantially hemispherical convex outer anchoring face 2 of the insertion cup 1.

To do this, the peripheral annular fixing structure 10 of the installation and orientation insert 7 has a radial thickness e3 substantially equal to or less than the thickness e1 of the radial shoulder d of the annular edge 4.

So as not to risk damaging the insertion cup 1, the installation and orientation insert 7 is advantageously made of plastic, preferably of polyethylene, which is an inexpensive material that is easy to machine.

Figure 15:
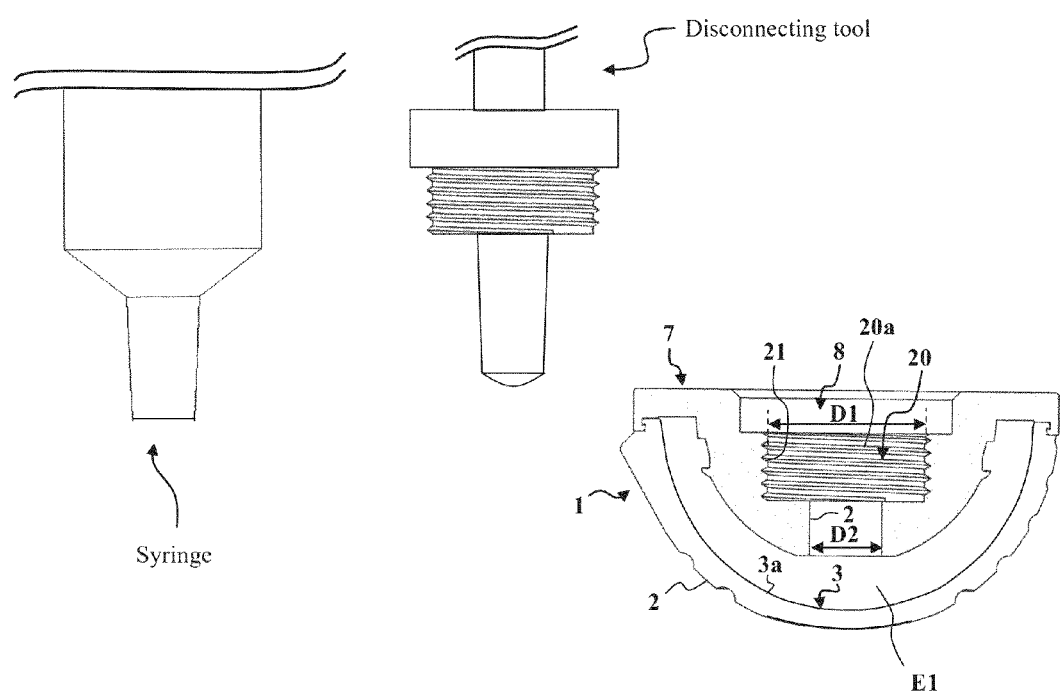
FIG. 15 is a sectional view of an insertion cup and of an installation and orientation insert once they have been assembled.

Within the context of the invention, the concave inner receiving face 3 can be a slide face 3a for receiving a movable articular insert, for example for an acetabulum with dual mobility. In this case, the slide face 3a is intended to receive a spherical movable articular insert (FIG. 15).

Figure 14:
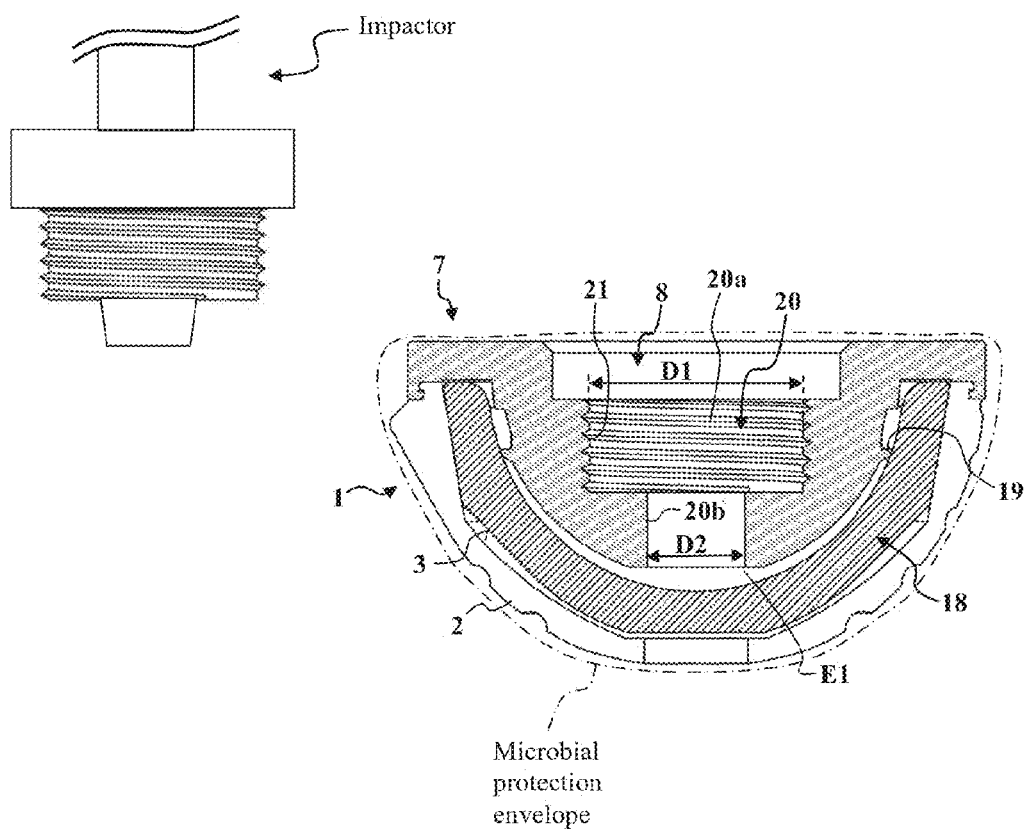
FIG. 14 is a sectional view of the elements from FIG. 13 once they have been assembled.

Still within the context of the invention, the concave inner receiving face 3 can be designed to receive a stationary articular insert 18, for example for an acetabulum with single mobility, as is illustrated in FIG. 14. The stationary articular insert 18 is immobilized in the insertion cup 1 by a conical engagement.

It will be seen more particularly in FIG. 14 that it is possible, at the place of manufacture, to carry out pre-assembly and sterile packaging of the articular insert 18 engaged in the insertion cup 1 with the installation and orientation insert 7 fixed to the insertion cup 1. This results in a pre-assembled unit ready for impaction by the surgeon, as a result of which the operating times can be reduced. In addition, the articular insert 18 is already fitted in the correct place in the insertion cup 1, which limits the risk of poor positioning thereof by the surgeon. This is particularly important when the articular insert 18 is made of ceramic, since poor positioning then very often leads to premature breaking of the ceramic.

It will be seen more particularly in FIG. 14 that the installation and orientation insert 7 has elastic means 19 for holding the ceramic articular insert 18 in the insertion cup 1. The elastic means 19 prevent any displacement of the articular insert 18 in the insertion cup 1 during transport, storage and handling of the pre-assembled insertion cup and articular insert 18.

So as not to risk damaging the ceramic articular insert 18 during impaction of the insertion cup 1, when the installation and orientation insert 7 is fixed to the insertion cup 1, the installation and orientation insert 7 comes into contact with the articular insert 18 only via the elastic holding means 19. It will be seen more particularly in FIG. 12 that the installation and orientation insert 7 is designed in such a way that a space E remains between the installation and orientation insert 7 and the articular insert 18. Therefore, no impaction shock is transferred to the ceramic articular insert 18, which is held in the bottom of the insertion cup 1 by the elastic means 19.

It will be seen more particularly in FIGS. 14 and 15 that the assembly structure 8 of the installation and orientation insert 7 comprises a fixation hole 20 with internal thread 21. The internal thread 21 permits the screwing of a corresponding threaded portion of the impactor (not shown).

After the impaction of the insertion cup 1 in the acetabular cavity of the pelvis of the patient, it is necessary to withdraw the installation and orientation insert 7. This withdrawal has to be performed without inducing stresses between the outer anchoring face 2 and the acetabular cavity of the pelvis of the patient, so as not to destroy the join made between them during the impaction.

A first solution to permit separation thus consists in the fixation hole 20 being a through-hole that is able to cooperate with a disconnecting tool having a threaded rod with a distal end designed to bear directly or indirectly against the concave inner receiving face 3 of the insertion cup 1 when the threaded rod is screwed into the through-hole. In FIGS. 14 and 15, the fixation hole 20 has a first portion 20a of diameter D1 and a second portion 20b of smaller diameter D2. The threaded rod of the disconnecting tool has an external diameter designed such that it can be screwed into the portion 20b of diameter D2 of the fixation hole 20.

A second solution permitting separation is one in which:
the installation and orientation insert 7 is designed such that a free space E1 remains between the installation and orientation insert 7 and the bottom of the concave inner receiving face 3 (FIG. 15) or, if appropriate, between the installation and orientation insert 7 and the articular insert 18 (FIG. 14), once the installation and orientation insert 7 is fixed to the outer annular receiving structure 6 of the insertion cup 1,
the installation and orientation insert 7 bears in a sealed manner across its connecting face 11 against the receiving face 9 of the outer annular receiving structure 6,
the fixation hole 20 is a through-hole via which the free space E1 is brought into communication with the outside and which is dimensioned for leaktight engagement of the end of a syringe.

In the case of FIGS. 14 and 15, the syringe end has an external diameter designed to engage in a leaktight manner in the portion of diameter D2 of the fixation hole 20.

A liquid such as water or physiological saline is thus injected at pressure into the free space E1 in order to induce a force of separation between the insertion cup 1 and the installation and orientation insert 7.

In order to obtain a sealed contact between the installation and orientation insert 7 and the insertion cup 1, use will preferably be made of the insertion cup 1 and the installation and orientation insert 7 that are illustrated in FIGS. 8 and 9.

Within the context of the present invention, when assembling the unit comprising the insertion cup 1 and an installation and orientation insert 7 (and if appropriate a stationary articular insert 18), it is important not to damage the annular receiving structure 6 and the peripheral annular fixing structure 10. In order to achieve a radial clamping of the peripheral annular fixing structure 10 on the outer annular receiving structure 6, it is necessary that the peripheral annular fixing structure 10 has diameter dimensions equal to or less than those of the outer annular receiving structure 6.

An assembly method involving expansion and subsequent shrinkage is therefore used, during which the installation and orientation insert 7 is heated so as to increase its dimensions, after which the peripheral annular fixing structure 10 is engaged around the receiving face 9 of the outer annular receiving structure 6, and, finally, the installation and orientation insert 7 is brought back to room temperature in order to reduce its dimensions.

Such a method permits assembly without blunting or damaging the one or more locking ribs 15a-15d or 17, which thus retain sharp edges for a stronger connection between the installation and orientation insert 7 and the insertion cup 1.

This method of manufacture by heating also makes it possible to avoid the abovementioned disadvantages of the method of manufacture by cooling as described in document WO 2006/040483 A1.

On its return to room temperature, a radial clamping of the peripheral annular fixing structure 10 on the outer annular receiving structure 6 is obtained. For assembling the unit illustrated in FIG. 14, it is possible, before fixing the installation and orientation insert 7 on the insertion cup 1, to insert an articular insert 18 in the concave inner receiving face 3 of the insertion cup 1.

It is then possible to proceed to a step of sterilization of the unit thus formed and packed in a microbial protection envelope. A satisfactory sterilization will be achieved by bombardment with gamma rays, preferably at a dose of between approximately 25 kGy and approximately 40 kGy.

It is expressly underlined that the method of manufacture and assembly of the units in FIGS. 14 and 15, by heating the installation and orientation insert 7 and then returning it to room temperature, can be used with an insertion cup 1 whose outer annular receiving structure 6 is not necessarily situated set back from the opening plane P. The method of manufacture may thus be the subject of protection independently of the position of the outer annular receiving structure 6 with respect to the opening plane P of the insertion cup 1.

The present invention is not limited to the embodiments that have been explicitly described, and instead it includes the variants and generalizations contained within the scope of the attached claims.

The invention claimed is:

1. Method for manufacturing a prosthetic hip acetabulum, comprising the steps of:
   a) providing an insertion cup (1) having a concave inner receiving face (3) with an opening face (5) contained in an opening place (P), having a convex outer anchoring surface (2) intended to come into contact with a bone of an acetabulum of a patient, and having an outer annular receiving structure (6),
   b) providing an installation and orientation insert (7), having an assembly structure (8) on which an impactor can be removably fixed, and having a peripheral annular fixing structure (10) designed to cooperate with a receiving face (9) of the outer annular receiving structure (6) by engaging externally around the outer annular receiving structure (6), wherein the peripheral annular fixing structure (10) has an outer diameter which is not greater than an outer diameter of a substantially hemispherical surface (S1) defined by the insertion cup (1), wherein the peripheral annular fixing structure (10) has a C-shaped cross-section which defines a connecting face (11) which is directed radially inwardly, and wherein the receiving face (9) of the outer annular receiving structure (6) is directed radially outwardly,
   c) heating the installation and orientation insert (7) in order to increase the dimensions thereof,
   d) engaging the peripheral annular fixing structure (10), externally around the receiving face (9) of the outer annular receiving structure (6), with the installation and orientation insert (7) not extending beyond the convex outer anchoring surface (2),
   e) bringing the installation and orientation insert (7) back to room temperature in order to reduce the dimensions thereof, so as to achieve a radial clamping of the peripheral annular fixing structure (10) on the outer annular receiving structure (6),
   wherein the outer annular receiving structure (6) comprises a continuous or interrupted peripheral radial shoulder (d) of an annular edge (4), and the receiving face (9) of the outer annular receiving structure (6) has a locking groove.

2. The method as claimed in claim 1, wherein, before engaging the installation and orientation insert (7) on the insertion cup (1), the method additionally comprises the supplementary step b1) of inserting an articular insert (18) in the concave inner receiving face (3) of the insertion cup (1).

3. The method as claimed in claim 2, wherein:
   the articular insert (18) is made of ceramic,
   the installation and orientation insert (7) has elastic means (19) for holding the articular insert (18) in the insertion cup (1),
   when the installation and orientation insert (7) is fixed to the insertion cup (1), the installation and orientation insert (7) comes into contact with the articular insert (18) only via the elastic means (19) for holding the articular insert (18) in the insertion cup (1).

4. The method as claimed in claim 2, additionally having a step f) during which the unit thus formed and packed in a microbial protection envelope is sterilized.

5. The method as claimed in claim 4, wherein the articular insert (18) is made of ceramic, and in that the step f) of sterilization is carried out by bombardment with gamma rays.

6. The method as claimed in claim 1, wherein the installation and orientation insert (7) is made of polyethylene.

7. The method as claimed in claim 1, wherein:
   the installation and orientation insert (7) has a continuous or interrupted peripheral annular fixing structure (10).

8. The method as claimed in claim 7, wherein:
   the locking groove of the receiving face (9) of the outer annular receiving structure (6) is an interrupted peripheral locking groove (14),
   the connecting face (11) of the peripheral annular fixing structure (10) of the installation and orientation insert (7) has a plurality of locking ribs (15a-15d) which are distributed peripherally and are designed so as to engage in the interrupted peripheral locking groove (14).

9. The method as claimed in claim 8, wherein said interrupted peripheral locking groove (14) or said continuous peripheral annular locking groove (16) of the outer annular receiving structure (6) has a height (h2) of between approximately 0.4 mm and approximately 3 mm.

10. The method as claimed in claim 7, wherein:
    either the receiving face (9) of the outer annular receiving structure (6) or the connecting face (11) of the peripheral annular fixing structure (10) has a continuous peripheral annular locking groove (16),
    the other of the connecting face (11) of the peripheral annular fixing structure (10) or the receiving face (9) of the outer annular receiving structure (6) has a continuous or interrupted peripheral annular locking rib (17) designed so as to engage in the continuous peripheral annular locking groove (16).

11. The method as claimed in claim 7, wherein:
    the peripheral radial shoulder (d) of the annular edge (4) has a thickness (e1) of between approximately 0.7 mm and approximately 1.2 mm,
    said interrupted peripheral locking groove (14) or said continuous peripheral annular locking groove (16) of the outer annular receiving structure (6) has a radial thickness (e2) of between approximately 0.2 mm and approximately 0.6 mm.

12. The method as claimed in claim 7, wherein the peripheral radial shoulder (d) of the annular edge (4) has a height (h1) of between approximately 1 mm and approximately 4 mm.

13. The method as claimed in claim 7, wherein the peripheral annular fixing structure (10) of the installation and orientation insert (7) has a radial thickness (e3) substantially equal to or less than the thickness (e1) of the radial shoulder (d) of the annular edge (4).

14. The method as claimed in claim 1, wherein the annular receiving structure (6) is external and is situated set back from the opening plane (P).

15. The method as claimed in claim 1, wherein the assembly structure (8) comprises a fixation hole (20) with internal thread (21) made in the installation and orientation insert (7), permitting the screwing of a corresponding threaded portion of the impactor.

16. The method as claimed in claim 15, wherein the fixation hole (20) is a through-hole able to cooperate with a disconnecting tool having a threaded rod which is able to be screwed into the through-hole and which has a distal end designed to bear directly or indirectly against the concave inner receiving face (3) of the insertion cup (1) when the threaded rod is screwed into the through-hole.

17. The method as claimed in claim 15, wherein:
the installation and orientation insert (7) is designed in such a way that a free space (E1) remains between the installation and orientation insert (7) and the bottom of the concave inner receiving face (3), or between the installation and orientation insert (7) and an articular insert (18), once the installation and orientation insert (7) is fixed to the outer annular receiving structure (6) of the insertion cup (1),
the installation and orientation insert (7) bears in a sealed manner across a connecting face (11) against the receiving face (9) of the outer annular receiving structure (6),
the fixation hole (20) is a through-hole via which the free space (E1) between the installation and orientation insert (7) and the bottom of the concave inner receiving face (3) or between the installation and orientation insert (7) and the articular insert (18), is brought into communication with the outside and which is dimensioned for leaktight engagement of the end of a syringe.

18. The method as claimed in claim 1, wherein the insertion cup (1) is made of metal.

19. The method as claimed in claim 1, wherein the insertion cup (1) is made of plastic.

\* \* \* \* \*